(12) United States Patent
Bogert (10) Patent No.: US 12,390,356 B2
(45) Date of Patent: Aug. 19, 2025

(54) RESUSCITATION BASE PELVIC BINDER

(71) Applicant: DIGNITY HEALTH, San Francisco, CA (US)

(72) Inventor: James N. Bogert, Chandler, AZ (US)

(73) Assignee: DIGNITY HEALTH, San Francisco, CA (US)

( * ) Notice: Subject to any disclaimer, the term of this patent is extended or adjusted under 35 U.S.C. 154(b) by 650 days.

(21) Appl. No.: 17/297,879

(22) PCT Filed: Nov. 27, 2019

(86) PCT No.: PCT/US2019/063753
§ 371 (c)(1),
(2) Date: May 27, 2021

(87) PCT Pub. No.: WO2020/113104
PCT Pub. Date: Jun. 4, 2020

(65) Prior Publication Data
US 2022/0031493 A1    Feb. 3, 2022

Related U.S. Application Data (60) Provisional application No. 62/772,972, filed on Nov. 29, 2018.

(51) Int. Cl.
*A61F 5/05* (2006.01)
(52) U.S. Cl.
CPC ..................... *A61F 5/05* (2013.01)
(58) Field of Classification Search
CPC ...... A61F 5/00; A61F 5/01; A61F 5/02; A61F 5/05; A61F 5/028; A61F 5/37;
(Continued)

(56) References Cited

U.S. PATENT DOCUMENTS 1,033,957 A * 7/1912 Shultz ...................... A41C 1/10
450/122
2,453,370 A    11/1948 Hittenberger
(Continued)

FOREIGN PATENT DOCUMENTS

EP    1637115 B1    3/2006
GB    765416         1/1957
(Continued)

*Primary Examiner* — Caitlin A Carreiro
(74) *Attorney, Agent, or Firm* — QUARLES & BRADY LLP (57) ABSTRACT

A device used for stabilizing the pelvis of a patient is provided. The device can include a first strap, a second strap, a fastening mechanism, a first supporting member, a second supporting member, and a first opening. The first strap can be configured to substantially surround the patient at a first location. The second strap can be configured to substantially surround the patient at a second location below the first strap. The first supporting member and second supporting member are coupled between the first strap and the second strap and can be configured to be positioned adjacent a first side and a second, opposite side, respectively, of the patient adjacent the anterior superior iliac spine. The first opening can be defined between the first strap, the second strap, the first supporting member, and the fastening mechanism to permit access to one of the femoral artery and the femoral vein.

21 Claims, 7 Drawing Sheets

(58) Field of Classification Search
CPC ... A61F 5/0193; A62B 35/00; A62B 35/0006;
A41C 1/08; A63B 21/4009; A61H 3/00;
B25J 9/0006; A41D 13/0007; A61B
5/6831
USPC .... 602/5, 12, 19, 23–24; 128/869, 870, 875,
128/876
See application file for complete search history.

(56) References Cited

U.S. PATENT DOCUMENTS

| | | | |
|---|---|---|---|
| 3,411,511 | A | 11/1968 | Marino |
| 4,836,194 | A | 6/1989 | Sebastian |
| 4,911,152 | A * | 3/1990 | Barnes ................ A61F 5/0585 602/23 |
| 6,500,137 | B1 | 12/2002 | Molino et al. |
| 6,544,232 | B1 * | 4/2003 | McDaniel ............ A61M 25/02 604/179 |
| 6,602,214 | B2 | 8/2003 | Heinz |
| 8,007,453 | B2 | 8/2011 | Richardson |
| 9,393,144 | B2 | 7/2016 | Ossur |
| 10,010,729 | B1 * | 7/2018 | Murphy ............ A62B 35/0018 |
| 2006/0135898 | A1 | 6/2006 | Richardson |
| 2006/0258967 | A1 | 11/2006 | Fujil |
| 2007/0197945 | A1 | 8/2007 | Islava |
| 2011/0034845 | A1 | 2/2011 | Polliack |
| 2012/0095379 | A1 * | 4/2012 | Hama .................. A61F 5/0193 602/23 |
| 2015/0173993 | A1 | 6/2015 | Walsh et al. |

FOREIGN PATENT DOCUMENTS

| | | |
|---|---|---|
| WO | 2000045756 | 8/2000 |
| WO | 2001037764 A1 | 5/2001 |
| WO | 2003017893 A1 | 3/2003 |

* cited by examiner

RESUSCITATION BASE PELVIC BINDER

CROSS REFERENCE TO RELATED APPLICATIONS

This application represents the national stage filing of PCT/US2019/063753, filed Nov. 27, 2019, which claims the benefit of U.S. Provisional Patent Application No. 62/772,972 filed on Nov. 29, 2018, the entire contents of which are incorporated herein by reference.

FIELD

The present application is directed to systems and methods for pelvic stabilization, including but not limited to a resuscitation base pelvic binder that permits access for surgical procedures, endovascular procedures, and/or attachment points for splinting while maintaining pelvic stabilization.

BACKGROUND

Pelvic stabilization is essential in blunt trauma cases because an unstable pelvic fracture can lead to complications such as internal bleeding, organ damage, and infection. For example, bleeding from pelvic fractures (often venous bleeding) can be severe and life threatening. Pelvic binders are therefore used in cases of trauma to stabilize the pelvis and prevent further fractures of the pelvic bone. Pelvic binders can help decrease potential movement of the pelvis and also help tamponade any bleeding. Currently, most pelvic binders for stabilizing the pelvis include a belt fastened with a required amount of force around a patient. The belt surrounds the pelvic bones to provide stability and compression.

In pelvic fracture cases, additional injuries are common and often require additional resuscitation strategies. For example, common surgical procedures in severe pelvic fracture cases include REBOA (Resuscitative Endovascular Balloon Occlusion of the Aorta), exploratory laparotomy, preperitoneal pelvic packing, Foley catheter insertion, and placement of lower extremity splints for femur fractures. Such procedures generally require access to the patient's lower extremities, lower abdomen, and/or femoral vessels. However, these body parts are generally blocked by currently available pelvic binders, thus making such interventions difficult or impossible with the pelvic binder in place. As a result, medical professionals often must remove the pelvic binder altogether or modify the pelvic binder by cutting and removing a portion of the binder to gain access to necessary body parts. But modifying a pelvic binder in this manner (or removing it altogether) can compromise the stability provided to pelvis and potentially increase bleeding. Furthermore, in some cases, cutting a pelvic binder can compromise sterility in the operating environment.

Therefore, it would be desirable to provide a pelvic binder that allows access to at least the femoral vessels and anterior abdomen while maintaining stability of the pelvis.

SUMMARY

Embodiments of the present invention overcome the drawbacks of previous systems and methods by providing systems and methods for stabilizing pelvic fractures in a way that permits access to at least the femoral vessels and anterior abdomen for surgical procedures.

In one aspect, the present disclosure provides a device used for stabilizing the pelvis of a patient. The device can comprise a first strap, a second strap, and a third strap. The first strap and the second strap can each include a first horizontal section and a second angled section. The first horizontal section can be configured to be positioned adjacent a back side of the patient. The second angled section can be configured to be positioned adjacent the front side of the patient. The third strap can be coupled to the second angled section of the first strap and the second strap.

In another aspect, the present disclosure provides a device used for stabilizing the pelvis of a patient. The device can comprise a first strap, a second strap, a fastening mechanism, a first supporting member, a second supporting member, and a first opening. The first strap can be configured to substantially surround the patient at a first location. The second strap can be configured to substantially surround the patient at a second location below the first strap. The first supporting member and second supporting member are coupled between the first strap and the second strap and can be configured to be positioned adjacent a first side and a second, opposite side, respectively, of the patient adjacent the anterior superior iliac spine. The first opening can be defined between the first strap, the second strap, the first supporting member, and the fastening mechanism to permit access to one of the femoral artery and the femoral vein.

Additional objectives, advantages and novel features will be set forth in the description which follows or will become apparent to those skilled in the art upon examination of the drawings and detailed description which follows.

Corresponding reference characters indicate corresponding elements among the view of the drawings. The headings used in the figures should not be interpreted to limit the scope of the claims.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

As used herein, unless otherwise specified or limited, "at least one of A, B, and C," and similar other phrases, are meant to indicate A, or B, or C, or any combination of A, B, and/or C. As such, this phrase, and similar other phrases can include single or multiple instances of A, B, and/or C, and, in the case that any of A, B, and/or C indicates a category of elements, single or multiple instances of any of the elements of the categories A, B, and/or C.

Disclosed herein is a resuscitation base pelvic binder for stabilizing a pelvis of a patient. Embodiments of the pelvic binder as illustrated in the figures are configured to for use in cases of trauma. In other embodiments, however, it should be appreciated that a pelvic binder can be configured for use for other medical cases which do not include trauma and which may include additional features not described herein. In still other embodiments, a pelvic binder could be used with alternate types of medical devices.

Generally, the pelvic binder of some embodiments may be worn by a patient (that is, positioned around the pelvis of the patient) to stabilize a pelvic fracture of the patient in a surgical environment, emergency environment, or non-surgical environment by a healthcare provider. The healthcare provider may be a surgeon, nurse, first responder, or other trained personnel. Furthermore, the pelvic binder of some embodiments may be used to stabilize a pelvic fracture to promote hemostasis without interfering with other resuscitative measures that may be needed, such as femoral vessel access, laparotomy, splinting, or preperitoneal pelvic packing. As one example, the pelvic binder can be fastened around the patient to stabilize the pelvis and can include angled straps and/or one or more openings to allow access to a plurality of locations on the patient, including the femoral vessels (e.g., the common femoral artery (CFA) or common femoral vein (CFV)), midline and anterior abdomen, and/or lower extremities, without binder removal or modification. The accessible region of the abdomen can include a region adjacent the pubic symphysis to permit access for surgical procedures such as a laparotomy and preperitoneal packing. In some embodiments, the pelvic binder can also include attachment mechanisms and can serve as a base to attach, for example, lower extremity long bone traction splints, restraints (e.g., for neurologically altered or combative patients), vascular access devices, or other attachments.

Figure 1:
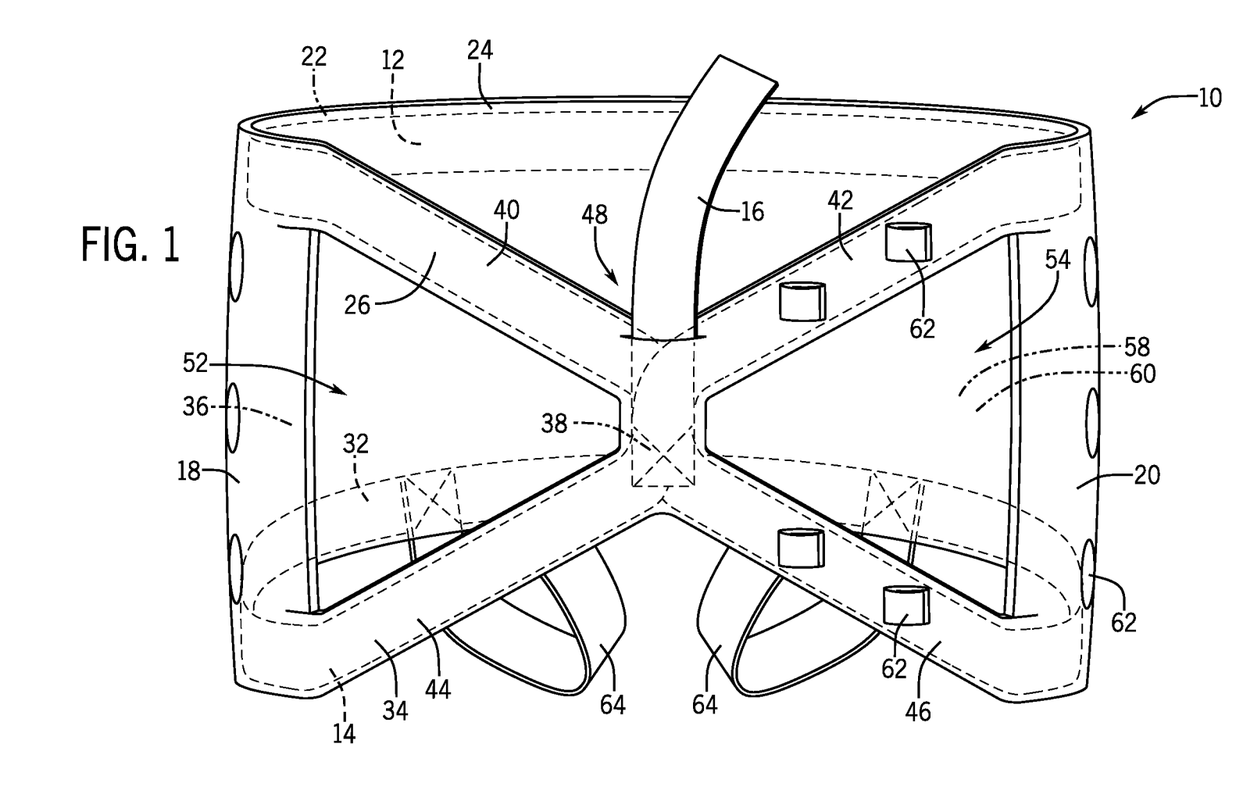
FIG. 1 is a perspective view of a pelvic binder according to some embodiments.
Figure 2:
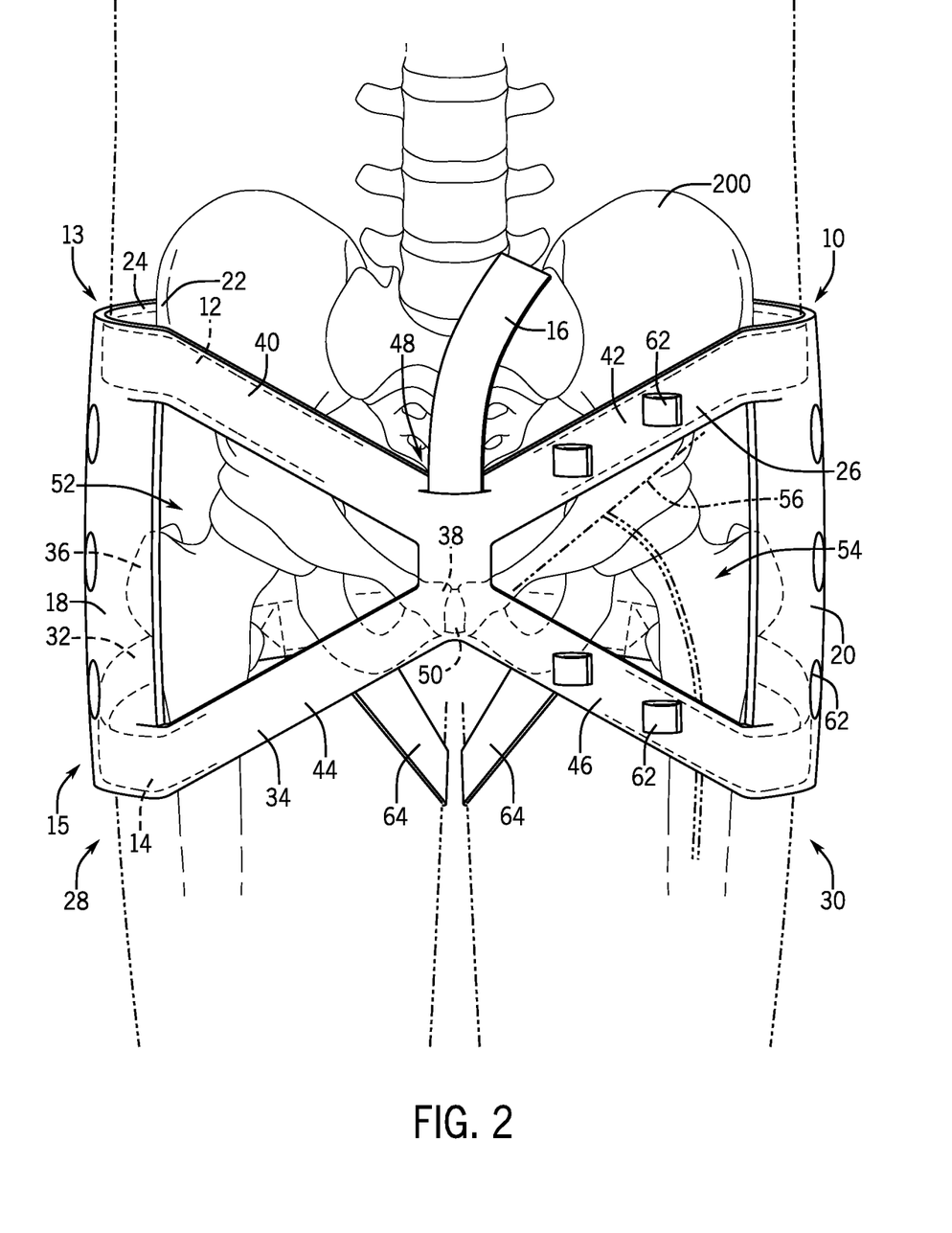
FIG. 2 is a perspective view of the pelvic binder of FIG. 1 around a pelvis of a patient, showing a portion of the patient's skeleton to illustrate a location of the pelvic binder during use.

Referring now to the Figures, and more particularly to FIG. 1, a pelvic binder 10 according to some embodiments is illustrated. FIG. 2 also illustrates the pelvic binder 10 of FIG. 1 around a pelvis 200 of a patient (e.g., showing a portion of the patient's skeleton to illustrate a location of the pelvic binder 10 during use). Generally, in some embodiments, the pelvic binder 10 may comprise a first strap 12, a second strap 14, a third strap 16, a first supporting member 18, and a second supporting member 20. The first strap 12 can be configured to substantially surround the patient at a first location 13 adjacent to the pelvis 200. For example, as shown in FIGS. 1 and 2, the first strap 12 can be configured to extend around the patient at or near the anterior superior iliac spine (ASIS) 22. Furthermore, the second strap 14 can be configured to surround the patient at a second location 15 adjacent to the pelvis (e.g., below the first strap 12), as shown in FIGS. 1 and 2. In some embodiments, the straps 12, 14 can be routed through a back panel.

In some embodiments, the first strap 12 can include a first horizontal section 24 and a second angled section 26. The first horizontal section 24 can be configured to be positioned adjacent a back side of the patient, and the second angled section 26 can be configured to be positioned adjacent a front side of the patient. As such, the first horizontal section 24 and the second angled section 26 can meet at points adjacent to a first and second side 28, 30 of the patient. Additionally, in some embodiments, the first horizontal section 24 and the second angled section 26 can form a single integral strap, or can be composed of two or more separate straps coupled together at the patient's sides 28, 30 (and/or other locations). Similarly, the second strap 14 can include a first horizontal section 32 configured to be positioned adjacent a back side of the patient and a second angled section 34 configured to be positioned adjacent a front side of the patient. The first horizontal section 32 and the second angled section 34 can meet adjacent the first and second sides 28, 30, and can be separate pieces coupled together or can form an integral strap. Furthermore, in some embodiments, as shown in FIGS. 1 and 2, the first horizontal section 24 and the first horizontal section 32 of the straps 12, 14 can be configured to be positioned vertically equidistant from the greater trochanters 36 of the patient. As such, the pelvic binder 10 is generally centered over the greater trochanters 36 to stabilize the pelvis.

As described above, the pelvic binder 10 can comprise the first supporting member 18 and the second supporting member 20. The first supporting member 18 can be coupled between the first strap 12 and the second strap 14 and can be configured to be positioned adjacent a first side 28 of the patient (e.g., a right side of the patient adjacent the ASIS 22) in a substantially vertical orientation. The second supporting member 20 can be coupled between the first strap 12 and the second strap 14 and can be configured to be positioned adjacent a second, opposite side 30 of the patient (e.g., a left side of the patient adjacent the ASIS 22) in a substantially vertical orientation. While the first and second sides 28, 30 are described and illustrated as being right and left sides of the patient, respectively, in some embodiments, the first and second sides may instead be left and right, respectively. In some embodiments, the back panel of the pelvic binder 10 can extend from the first supporting member 18 to the second supporting member 20. Additionally, in some embodiments, the respective first horizontal sections 24, 32 and second angled sections 26, 34 of the first strap 12 and the second strap 14 can meet at the first supporting member 18 along the first side 28 and the second supporting member 20 along the second side 30, respectively. Furthermore, the first supporting member 18 and the second supporting member 20 can be sufficiently rigid to maintain a vertical distance between the first strap 12 and the second strap 14 for proper positioning of the pelvic binder 10 on the patient.

Furthermore, the pelvic binder 10 can be tightened or loosened around a patient by adjusting the third strap 16. For example, in some embodiments, the second angled section 26, 34 of each strap 12, 14 can each be coupled to the third strap 16 to provide adjustable structural stability to a fractured pelvis. More specifically, in some embodiments, the third strap 16 can be removably (or permanently) coupled to at least one of the first strap 12 and the second strap 14 to join the straps 12, 14 together and act as a fastening mechanism of the pelvic binder 10. The third strap 16 can also be adjustable and configured to pull the first strap 12 and the second strap 14 towards each other to form the second angled section 26, 34. For example, the third strap 16 can be a single tension strap that cinches together the first strap 12 and the second strap 14. This adjustment can tighten the pelvic binder 10 around the pelvis, thus providing structural stability. Furthermore, the adjustability allows for stabilizing pelvic bones of different shapes and sizes according to the size and age of the patient. Additionally, the third strap 16 can generally be configured to be positioned adjacent to and extend below the pubic tubercles 38 of the patient to permit access to the abdomen for medical procedures, as further described below. In some embodiments, the third strap 16 can generally be vertical in orientation and centered over the pubic symphysis. In some embodiments, other adjustable fasteners may be contemplated as part of the third strap 16 (e.g., belt buckles, buckle clips with adjustable straps, pulley systems, clicking belt locks, or other fastening mechanisms).

As shown in FIG. 1, the third strap 16 generally separates two portions of the second angled sections 26, 34 of the first strap 12 and the second strap 14. More specifically, with respect to the first strap 12, the second angled section 26 can include a first portion 40 that extends diagonally from the first supporting member 18 to the third strap 16 and a second portion 42 that extends diagonally from the second supporting member 20 to the third strap 16. The first portion 40 and the second portion 42 are each configured to be angled downward from a respective supporting member 18, 20 to the third strap 16, thus generally forming a "v" shape.

With respect to the second strap 14, the second angled section 34 can include a first portion 44 that extends diagonally from the first supporting member 18 to the third strap 16 and a second portion 46 that extends diagonally from the second supporting member 20 to the third strap 16. The first portion 44 and the second portion 46 are each configured to be angled upward from a respective supporting member 18, 20 to the third strap 16, thus generally forming an inverted "v" shape. In some embodiments, however, the second angled section of the second strap 14 may be substantially horizontal, so that only the first strap 12 (e.g., the top strap) includes angled portions. In such embodiments, the third strap 16 only cinches down the first strap 12 toward the second strap 14 (e.g., rather than cinching both the first strap 12 and the second strap 14 toward each other).

Generally, the straps 12, 14, 16, and the supporting members 18, 20 can enable the pelvic binder 10 to distribute loads across, for example, its superior and inferior borders (e.g., the first strap 12 and the second strap 14) to provide sufficient pelvic compression while still leaving areas of pelvic region accessible for medical procedures. For example, as shown in FIGS. 1 and 2, the pelvic binder 10 can include an open region 48 partially defined between the first portion 40 and the second portion 42 of the first strap 12 (e.g., inside the "v" shape). This open region 48 can permit access to the abdomen adjacent the pubic symphysis 50 of the patient for, e.g., a midline laparotomy procedure or preperitoneal packing. For example, the general access area needed for such procedures includes a superior border adjacent the umbilicus, an inferior border adjacent the pubic symphysis 50, and lateral borders adjacent the ASIS 22. The open region 48 provides access for such procedures within these borders while maintaining stability of the pelvis, that is, without requiring modification of the pelvic binder 10, such as loosening, moving, or removing any straps. Accordingly, the pelvic binder 10 generally does not extend above or over the pubic symphysis 50 to allow access to the open region 48. Furthermore, access to the urethra for Foley catheter insertion can be available beneath the pelvic binder 10.

Additionally, in some embodiments, the pelvic binder 10 can include a first opening 52 defined between the first strap 12, the second strap 14, the third strap 16, and the first supporting member 18. The pelvic binder 10 can also include a second opening 54 defined between the first strap 12, the second strap 14, the third strap 16, and the second supporting member 20. The openings 52, 54 can each permit access to the common femoral artery (CFA) or the common femoral vein (CFV) along the first side 28 or the second side 30 of the patient, respectively. For example, the general access area needed for reliable CFA/CFV access includes a superior border adjacent the inguinal ligaments 56, medial borders adjacent the pubic tubercles 38, and lateral borders adjacent the ASIS 22. The openings 52, 54 provide access for such procedures within these borders while maintaining stability of the pelvis, that is, without requiring modification of the pelvic binder 10, such as loosening, moving, or removing any straps or material. For example, FIG. 1 illustrates accessible locations 58, 60 of the femoral artery and femoral vein, respectively, within the second opening 54. Furthermore, such vascular access can be obtained by a medical professional or an autonomous device (as further described below).

Vascular access during pelvic stabilization can be beneficial to permit, for example, central venous line insertion or REBOA (Resuscitative Endovascular Balloon Occlusion of the Aorta) procedures. For example, REBOA procedures can help manage abdominal, pelvic, or lower extremity bleeding and require rapidly placing a catheter into the femoral artery. The pelvic binder 10 of some embodiments, by providing the openings 52, 54, is thus REBOA-compatible. Some conventional binders, while thin enough to provide pelvic stabilization as well as access to the some portions of the abdomen, extend across the greater trochanters for such stabilization and, thus, are not REBOA-compatible because they obscure access to the femoral vessels. Additionally, in some embodiments, to better accommodate interventional radiology procedures (such as REBOA, angiography, or endovascular embolization), the pelvic binder 10 can be made of radiolucent material.

In some embodiments, one or more of the first strap 12, the second strap 14, the first supporting member 18, and the second supporting member 20 can include one or more attachment mechanisms 62 configured to couple an attachment to the pelvic binder 10. For example, these attachment mechanisms 62 can act as docking sites for different attachments (such as adjuncts for resuscitation). As such, the pelvic binder 10 can serve as a supporting base for certain attachments.

As one example, one or more attachment mechanisms 62 can be coupled to or integral with the first strap 12 and/or the second strap 14 and can be configured to be coupled to a vascular access device (not shown). An example vascular access device is described in U.S. Provisional Patent Application No. 62/816,549, the entire contents of which is incorporated herein by reference. The vascular access device can be coupled to the pelvic binder 10 via one or more attachment mechanisms 62 to extend over one of the openings 52, 54 in order to automatically or semi-automatically access the femoral artery 58 or the femoral vein 60 of the patient. By permitting use of an autonomous vascular access device fixed to the pelvic binder 10, venous or arterial access can be automated (or at least semi-automated) while healthcare providers work on other aspects of the patient's resuscitation. Additionally, vascular devices manually placed by health care workers can be secured to the pelvic binder 10 via the attachment mechanism 62. Securing these devices to the pelvic binder 10 can reduce the risk of inadvertent removal or dislodgement during patient transport or repositioning.

As another example, one or more attachment mechanisms 62 can be coupled to one of the first supporting member 18 and/or the second supporting member 20 and can be configured to be coupled to a femoral traction splint (not shown). A femoral traction splint can thus be anchored to the pelvic binder 10 via the attachment mechanisms 62 and can naturally stabilize a bone of the patient (e.g., broken bones in the patient's lower extremities). A splint may also provide stability for the patient's leg during a surgical procedure.

In yet another example, one or more attachment mechanisms 62 can be coupled to any of the above elements of the pelvic binder 10 and can be configured to be coupled to one or more restraints. For example, restraints can be coupled to the attachment mechanisms 62 and further coupled to a hospital bed or other structure to help restrain the patient.

The attachment mechanisms 62 can also be configured to be coupled to other attachments not specifically described herein. In some embodiments, the attachment mechanisms 62 can be clips, buttons, snaps, buckles, hooks, or other fasteners. Furthermore, in some embodiments, the attachment mechanisms 62 may act as universal attachment mechanisms (e.g., be uniform in type, size, and/or shape) so that any potential attachment (e.g., vascular access device, splint, restraints, etc.) only need an equivalent mating attachment mechanism to be compatible with the pelvic binder 10. In other embodiments, different attachment mechanisms 62 may be coupled to different portions of the pelvic binder 10.

In some embodiments, the pelvic binder 10 can further comprise one or more loops 64 coupled to and extending below the second strap 14 (e.g., the horizontal section 32 of the second strap 14). For example, two loops 64 can be coupled to the second strap 14 and configured to wrap around the buttocks of the patient (e.g., similar to a jock strap). In some embodiments, each loop 64 can be permanently or removably coupled to the horizontal section 32 of the second strap 14 (e.g., a posterior end of the second strap 14) and permanently or removably coupled to an anterior portion of the second strap 14. As a result, the loops 64 can provide additional stabilization and, in some embodiments, can also prevent of migration of a traction splint attachment. For example, in a trauma setting, a splint on the leg should provide traction (e.g., pulling the foot down away from the pelvis). This force would generally cause a pelvic binder to ride up higher on the patient, rather than allow the binder in a desired position for pelvic stability. In some embodiments, the loops 64 can prevent the pelvic binder 10 from riding up higher on the patient by anchoring the pelvic binder 10 to the buttocks.

Accordingly, the pelvic binder 10 of FIGS. 1 and 2 can provide compression for pelvic fractures and is configured to distribute loads across its superior and inferior borders in order to leave body regions free for CFV or CFA access or abdominal access for midline laparotomies or preperitoneal packing. The pelvic binder 10 can further serve as a base for a traction splint (e.g., for femur fractures), an autonomous vascular access device (to assist vascular access), restraints, and/or other attachments.

Figure 3:
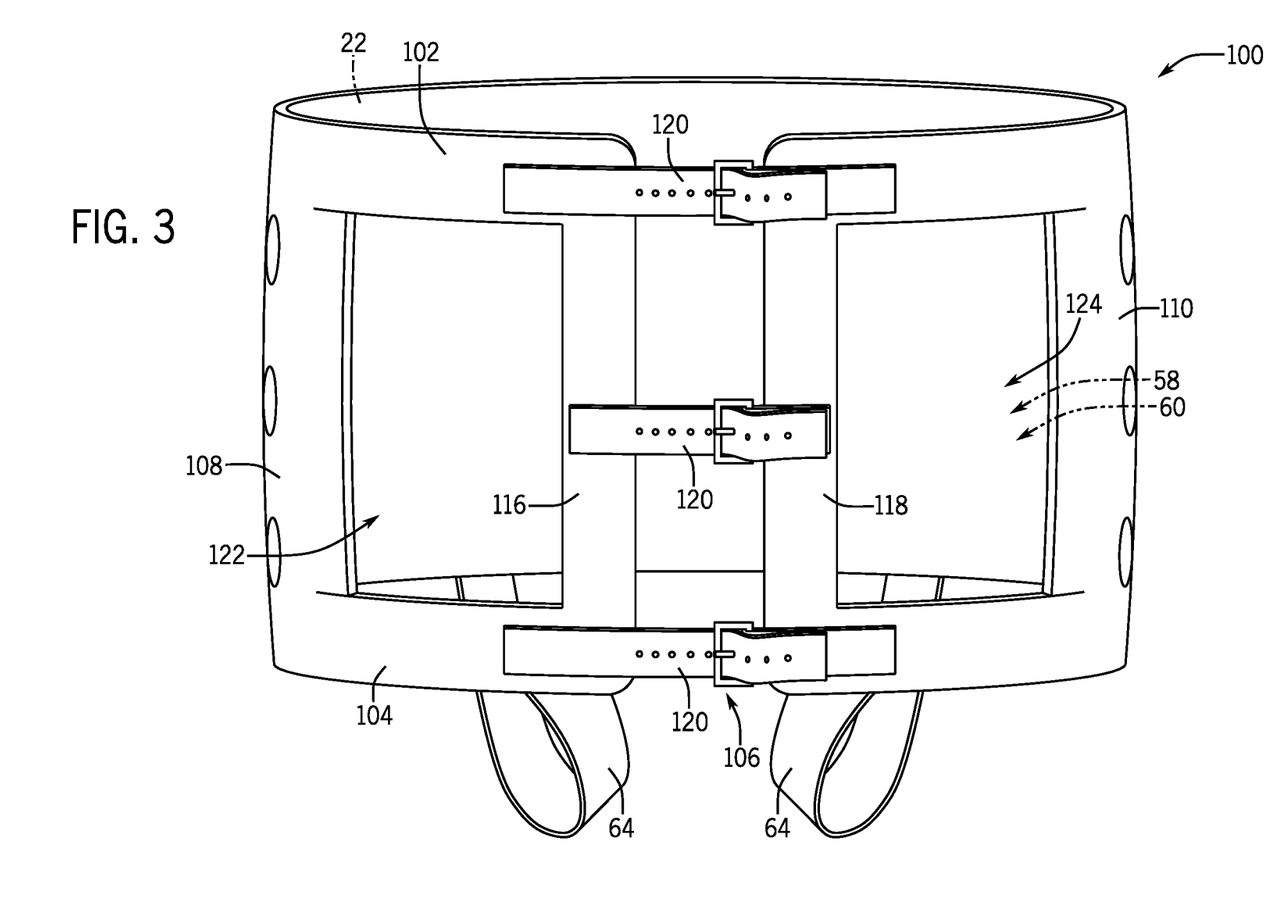
FIG. 3 is a perspective view of another pelvic binder according to some embodiments.
Figure 4:
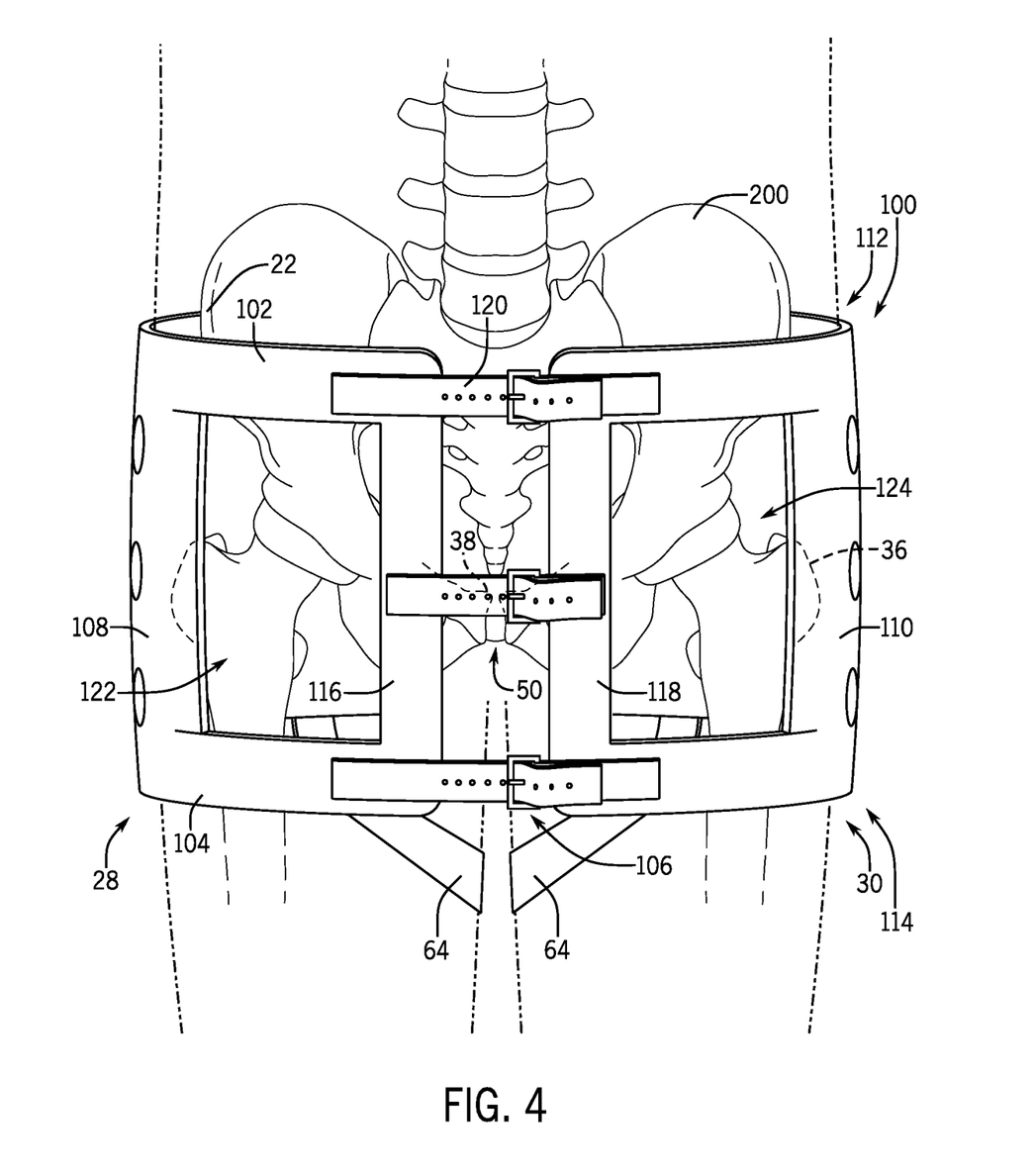
FIG. 4 is a perspective view of the pelvic binder of FIG. 3 around a pelvis of a patient, showing a portion of the patient's skeleton to illustrate a location of the pelvic binder during use.

Referring now to FIG. 3, a pelvic binder 100 according to another embodiment of the present disclosure is shown. For example, the pelvic binder 100 can be fastened around the pelvis 200, as shown in FIG. 4. Similar to the pelvic binder 10 of FIGS. 1 and 2, the pelvic binder 100 can be adjusted to allow for variable pelvic region sizes and can provide stabilization for a variety of pelvic fractures while permitting access to various regions for medical procedures. For example, the pelvic binder 100 can be fastened around the patient to allow access to a plurality of locations on the patient including the femoral vessels, anterior abdomen, and/or lower extremities.

In some embodiments, the pelvic binder 100 can comprise a first strap 102, a second strap 104, a fastening mechanism 106, a first supporting member 108, and a second supporting member 110. Generally, the first strap 102 and the second strap 104 can be configured to substantially surround the patient at a first location 112 and a second location 114, respectively, adjacent the pelvis 200. Also, the first strap 102 and the second strap 104 can be fastened around the pelvis 200 by the fastening mechanism 106. More specifically, the fastening mechanism 106 can pull each respective strap 102, 104 toward itself to tighten the pelvic binder 100 around the pelvis.

In some embodiments, the first strap 102 can extend around the pelvis in a substantially horizontal orientation and can be configured to extend around the patient adjacent the ASIS 22. The first strap 102 can include a single, integral strap, or can include two or more straps coupled together (e.g., at the first supporting member 108, the second supporting member 110, and/or other locations). Similarly, the second strap 104 can extend around the pelvis in a substantially horizontal orientation and can be located below the first strap 102. The second strap 104 can include a single, integral strap, or can include two or more straps coupled together (e.g., at the first supporting member 108, the second supporting member 110, and/or other locations). In some embodiments, the first strap 102 and the second strap 104 can be configured to be positioned vertically equidistant from the greater trochanters 36 of the patient. As such, the pelvic binder 100 is generally centered over the greater trochanters 36 to stabilize the pelvis.

As described above, the pelvic binder 100 can include the first supporting member 108 and the second supporting member 110. More specifically, the first supporting member 108 can be coupled between the first strap 102 and the second strap 104 and can be configured to be positioned adjacent the first side 28 of the patient (e.g., a right or left side of the patient adjacent the ASIS 22). The second supporting member 110 can be coupled between the first strap 102 and the second strap 104 and can be configured to be positioned adjacent the second, opposite side 30 of the patient (e.g., the opposite left or right side of the position adjacent the ASIS 22). Accordingly, as shown in FIGS. 3 and 4, the first supporting member 108 and the second supporting member 110 can be substantially vertical in orientation. In some embodiments, the first supporting member 108 and the second supporting member 110 can each be coupled to or integral with a back panel of the pelvic binder 10 (that is, along the posterior of the pelvic binder 10) and the first strap 102 and the second strap 104 can extend from the first supporting member 108 to the second supporting member 110 along the anterior of the pelvic binder 10.

Furthermore, the fastening mechanism 106 can fasten together the first and second straps 102, 104. In some embodiments, the fastening mechanism 106 can include a first member 116, a second member 118, and one or more adjustable fasteners 120. The first member 116 can be coupled between the first strap 102 and the second strap 104 on the first side 28 of the patient (e.g., to the right of the patient's midline). The second member 118 can be coupled between the first strap 102 and the second strap 104 on the second side 30 of the patient (e.g., to the left of the patient's midline). For example, the first strap 102 can be configured to wrap around the patient and terminate at the first and second members 124, 126. Similarly, the second strap 104 can be configured to wrap around the patient and terminate at the first and second members 124, 126.

The adjustable fastener 120 can be coupled to the first member 116 and the second member 118 and configured to pull the first member 116 towards the second member 118 to tighten and secure the pelvic binder 100 around the pelvis 200. The adjustable fastener 120 can therefore adjust the pelvic binder 100 so that it can be configured for a variety of sizes of pelvic bones and pelvic fractures. In some embodiments, the adjustable fastener 120 may be a belt-like structure (e.g., with two straps each coupled to a respective member 116, 118 and a buckle configured to tighten and secure the straps together). However, other adjustable fasteners may be contemplated in some embodiments (e.g., buckle clips with adjustable straps, pulley systems, clicking belt locks, or other fastening mechanisms). Furthermore, while three adjustable fasteners 120 are shown in FIGS. 3 and 4, some embodiments may include a single fastener 120, two fasteners 120, or more than three fasteners 120.

Generally, the straps 102, 104, the supporting members 108, 110, and the fastening mechanism 106 can enable the pelvic binder 100 to distribute loads across, for example, its superior and inferior borders (e.g., the first strap 102 and the second strap 104) to provide sufficient pelvic compression while still leaving areas of the pelvic region accessible for medical procedures. For example, the pelvic binder 100 can include a first opening 122 defined between the first strap 102, the second strap 104, the first supporting member 108, and the fastening mechanism 106. Access to one of the femoral artery 58 and the femoral vein 60 along the first side 28 of the patient can be permitted via the first opening 122. The pelvic binder 100 can further comprise a second opening 124 defined between the first strap 102, the second strap 104, the second supporting member 110, and the fastening mechanism 106. The second opening 124 can permit access to one of the femoral artery 58 and the femoral vein 60 along the second side 30 of the patient.

The openings 122, 124 can be sized to encompass the general access area needed for reliable CFA/CFV access (as described above), while still permitting the pelvic binder 100 to maintain stability of the pelvis without requiring modification of the pelvic binder 100. Furthermore, such vascular access can be obtained by a medical professional or an autonomous vascular device configured to be attached to the pelvic binder 100 or the patient directly. Accordingly, the pelvic binder 100 can permit vascular access for, for example, central venous line insertion or REBOA procedures, as described above. Additionally, to better accommodate interventional radiology procedures (such as REBOA), the pelvic binder 10 can be made of radiolucent material in some embodiments.

The pelvic binder 100 can also provide abdominal access for midline laparotomies or preperitoneal packing while maintaining stability of the pelvis. For example, one of the plurality of fasteners 120 can be unfastened for such access without compromising the structural stability of the pelvis, as the other fasteners 120 can remain fastened to provide sufficient pressure for such stability. In one example, access to perform a laparotomy or pelvic packing can be provided by unfastening the top-most fastener 120 while keeping the middle and lower fasteners 120 secured. In another example, access to place a Foley catheter can be provided by unfastening the bottom-most fastener 120 while keeping the middle and upper fasteners 120 secured.

Additionally, one or more of the first strap 102, the second strap 104, the first supporting member 108, and the second supporting member 110 can include one or more attachment mechanisms (not shown) configured to couple an attachment to the pelvic binder 100, similar to that described above with respect to the attachment mechanisms 62 of pelvic binder 10 of FIGS. 1 and 2. As such, the pelvic binder 100 can be attached to, for example, a traction splint, an autonomous vascular access device, restraints, and/or other attachments.

Accordingly, the pelvic binder 100 of FIGS. 3 and 4 can provide compression for pelvic fractures and is configured to distribute loads across its superior and inferior borders in order to leave body regions free for CFV or CFA access or abdominal access for midline laparotomies or preperitoneal packing. The pelvic binder 100 can further serve as a base for a traction splint (e.g., for femur fractures), an autonomous vascular access device (to assist vascular access), restraints, and/or other attachments.

Figure 5:
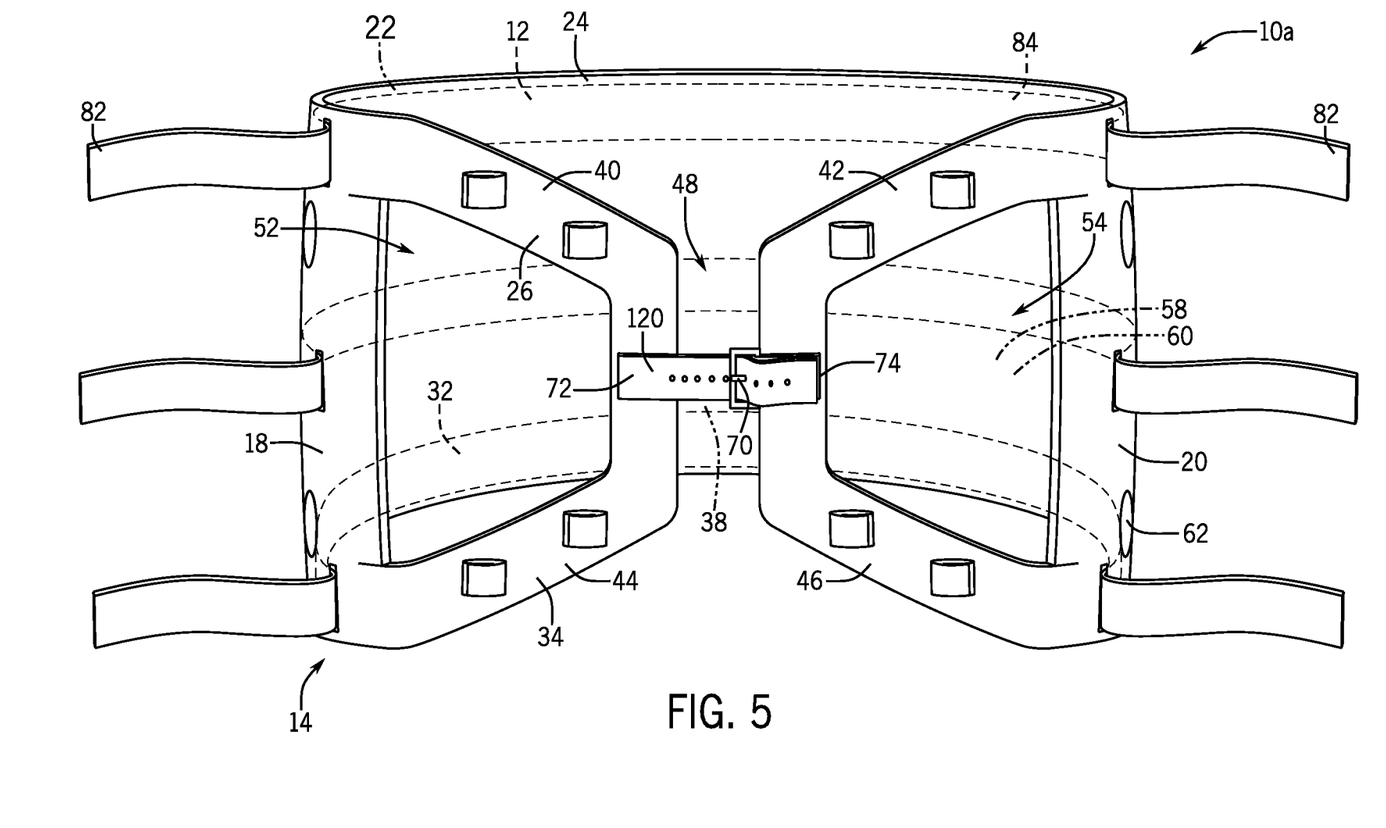
FIG. 5 is a perspective view of another pelvic binder according to some embodiments.
Figure 6:
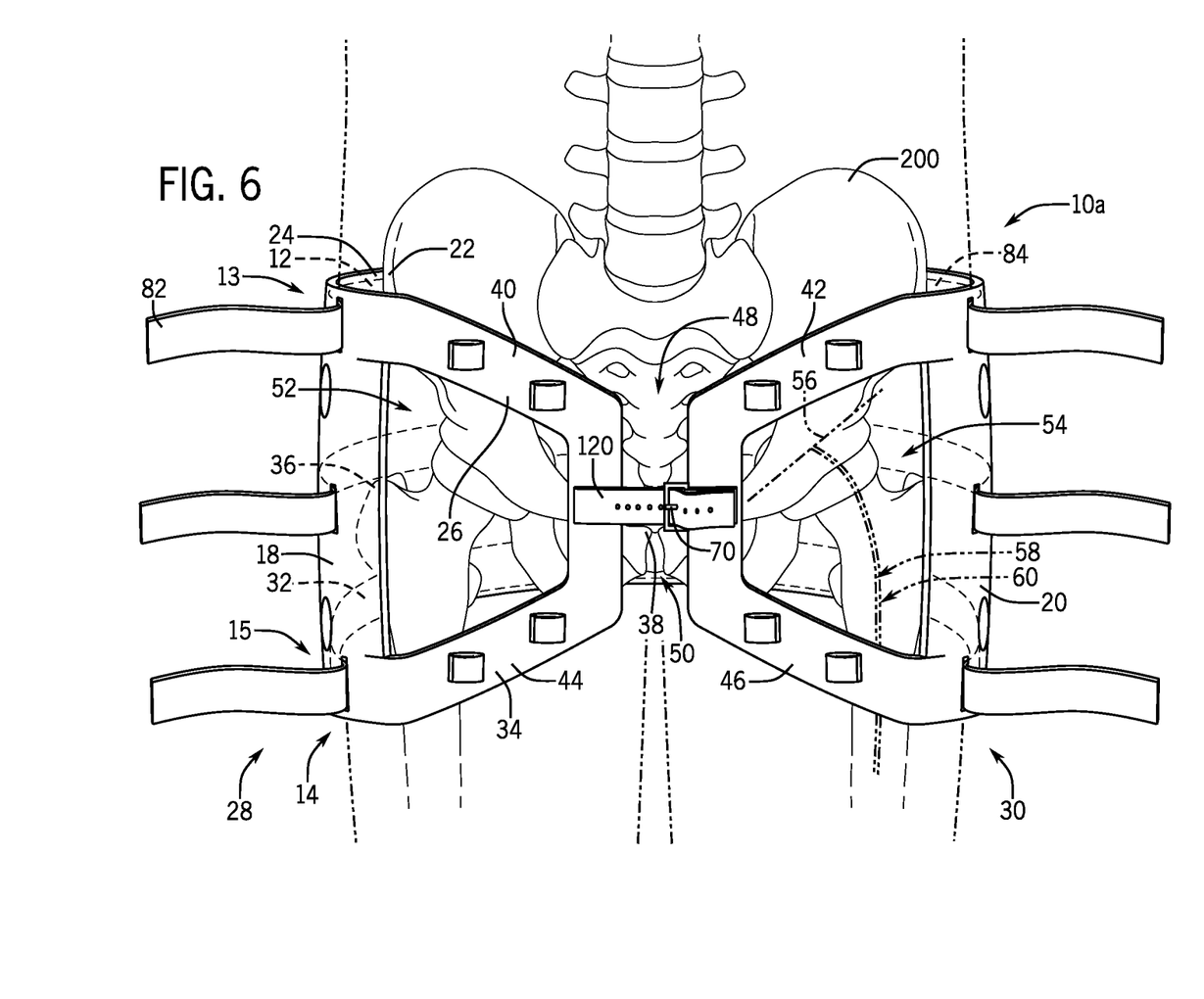
FIG. 6 is a perspective view of the pelvic binder of FIG. 5 around a pelvis of a patient, showing a portion of the patient's skeleton to illustrate a location of the pelvic binder during use.
Figure 7:
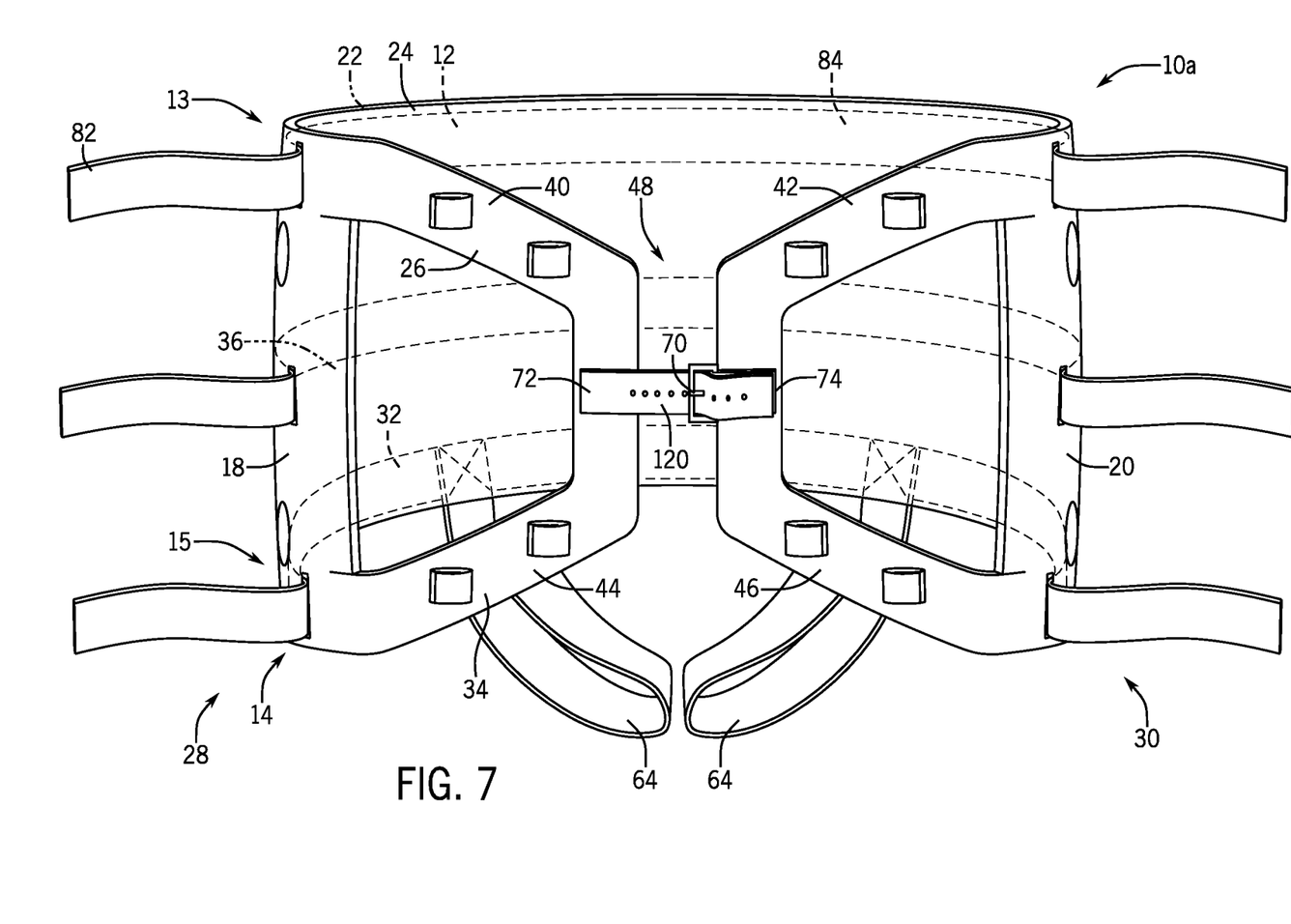
FIG. 7 is another perspective view of the pelvic binder of FIG. 5, according to some embodiments.

Referring now to FIGS. 5-7, a pelvic binder 10a, according to some embodiments, is illustrated. FIG. 6 illustrates the pelvic binder 10a around a pelvis 200 of a patient (e.g., showing a portion of the patient's skeleton to illustrate a location of the pelvic binder 10a during use). Generally, in some embodiments, the pelvic binder 10a may comprise a first strap 12, a second strap 14, a fastening member 70, a first supporting member 18, and a second supporting member 20. The first strap 12 can be configured to substantially surround the patient at a first location 13 adjacent to the pelvis 200. For example, as shown in FIGS. 5 and 6, the first strap 12 can be configured to extend around the patient at or near the anterior superior iliac spine (ASIS) 22. Furthermore, the second strap 14 can be configured to surround the patient at a second location 15 adjacent to the pelvis (e.g., below the first strap 12), as shown in FIGS. 5-7, similar to the second strap 12 of the pelvic binder 10 of FIGS. 1 and 2. Additionally, in some embodiments, the straps 12, 14 can be routed through a back panel.

In some embodiments, the first strap 12 can include a first horizontal section 24 and a second angled section 26. The first horizontal section 24 can be configured to be positioned adjacent a back side of the patient, and the second angled section 26 can be configured to be positioned adjacent a front side of the patient. As such, the first horizontal section 24 and the second angled section 26 can meet at points adjacent to a first and second side 28, 30 of the patient. Additionally, in some embodiments, the first horizontal section 24 and the second angled section 26 can form a single integral strap, or can be composed of two or more separate straps coupled together at the patient's sides 28, 30 (and/or other locations). Similarly, the second strap 14 can include a first horizontal section 32 configured to be positioned adjacent a back side of the patient and a second angled section 34 configured to be positioned adjacent a front side of the patient. The first horizontal section 32 and the second angled section 34 can meet adjacent the first and second sides 28, 30, and can be separate pieces coupled together or can form an integral strap. Furthermore, in some embodiments, as shown in FIG. 6, the first horizontal section 24 and the first horizontal section 32 of the straps 12, 14 can be configured to be positioned vertically equidistant from the greater trochanters 36 of the patient. As such, the pelvic binder 10a is generally centered over the greater trochanters 36 to stabilize the pelvis.

Referring still to FIGS. 5-7, similar to the supporting members 18, 20 of the pelvic binder 10 of FIGS. 1 and 2, the first supporting member 18 can be coupled between the first strap 12 and the second strap 14 and can be configured to be positioned adjacent a first side 28 of the patient (e.g., a right side of the patient adjacent the ASIS 22) in a substantially vertical orientation. The second supporting member 20 can be coupled between the first strap 12 and the second strap 14 and can be configured to be positioned adjacent a second, opposite side 30 of the patient (e.g., a left side of the patient adjacent the ASIS 22) in a substantially vertical orientation. Additionally, in some embodiments, the respective first horizontal sections 24, 32 and second angled sections 26, 34 of the first strap 12 and the second strap 14 can meet at the first supporting member 18 along the first side 28 and the second supporting member 20 along the second side 30, respectively. Furthermore, the first supporting member 18 and the second supporting member 20 can be sufficiently rigid to maintain a vertical distance between the first strap 12 and the second strap 14 for proper positioning of the pelvic binder 10 on the patient.

Furthermore, the fastening member 70 can act as a fastening mechanism of the pelvic binder 10a to fasten together the first and second straps 12, 14. More specifically, the pelvic binder 10a can be tightened or loosed around a patient by adjusting the fastening member 70, and the second angled sections 26, 34 of the straps 12, 14 can each be coupled to the fastening member 70 to provide adjustable structural stability to a fractured pelvis. For example, in some embodiments, the fastening member 70 can include a first member 72, a second member 74, and one or more adjustable fasteners 120. The first member 72 can be coupled between the first strap 12 and the second strap 14 on the first side 28 of the patient (e.g., to the right of the patient's midline). The second member 74 can be coupled between the first strap 12 and the second strap 14 on the second side 28 of the patient (e.g., to the left of the patient's midline). The adjustable fastener 120 can be similar to the adjustable fastener 120 as described above with respect to FIGS. 3 and 4 and can be configured to pull the members 72, 74 toward each other when tightened. This adjustment can tighten the pelvic binder 10a around the pelvis, thus providing structural stability. Furthermore, the adjustability allows for stabilizing pelvic bones of different shapes and sizes according to the size and age of the patient. Additionally, the fastening member 70 can generally be configured to be positioned adjacent to and extend below the pubic tubercles 38 (or pubic symphysis 50) of the patient to permit access to the abdomen for medical procedures, as further described below.

As shown in FIGS. 5-7, the fastening member 70 generally separates two portions of the second angled sections 26, 34 of the first strap 12 and the second strap 14. More specifically, with respect to the first strap 12, the second angled section 26 can include a first portion 40 that extends diagonally from the first supporting member 18 to the first member 72 of the fastening member 70 and a second portion 42 that extends diagonally from the second supporting member 20 to the second member 74 of the fastening member 70. The first portion 40 and the second portion 42 are each configured to be angled downward from a respective supporting member 18, 20 to the fastening member 70, thus generally forming a "v" shape. With respect to the second strap 14, the second angled section 34 can include a first portion 44 that extends diagonally from the first supporting member 18 to the first member 72 of the fastening member 70 and a second portion 46 that extends diagonally from the second supporting member 20 to the second member 74 of the fastening member 70. The first portion 44 and the second portion 46 are each configured to be angled upward from a respective supporting member 18, 20 to the fastening member 70, thus generally forming an inverted "v" shape. In some embodiments, however, the second angled section of the second strap 14 may be substantially horizontal, so that only the first strap 12 (e.g., the top strap) includes angled portions.

The pelvic binder 10a can further include one or more adjustable straps 84 configured to extend around the back of the patient and act as a secondary fastening mechanism. As shown in FIGS. 5-7, the straps 84 can extend through the supporting members 18, 20 along the sides of the pelvic binder 10a as well as the back panel. When the pelvic binder 10a is placed around a patient, a medical professional can pull tail portions 82 of the straps 84 to remove extra slack in the straps 84 around the patient's back for tightening the pelvic binder 10a. While three adjustable straps 84 are shown in FIGS. 5-7, some embodiments can include one, two, or more than three adjustable straps 84.

The straps 84 can contribute to tightening of the pelvic binder 10a in addition to the above-described fastening member 70. As a result, the pelvic binder 10a can include both posterior tightening (via the posterior straps 84) and anterior tightening (via the anterior fastening member 70) to achieve proper compression for pelvic stabilization. In one example, the straps 84 can be tightened first to remove slack in the back, and then the fastening member 70 can be tightened in the front. In addition, as the pelvic binder 10a is tightened from the posterior and anterior, the angled sections 26, 34 of the first and second straps 12, 14 can be pulled together rather than cinched inward (as they are in the pelvic binder 10 of FIGS. 1-2). As a result, in some embodiments, the angled sections 26, 34 can be substantially rigid (e.g., more rigid than those of the pelvic binder 10 of FIGS. 1-2). In another example, the straps 84 can be used as a secondary tightening mechanism when the fastening member 70 is tightened as much as possible and the overall circumference of the pelvic binder 10a is still too large (that is, the pelvic binder 10a is still not tight enough around the patient's pelvis for proper compression and stabilization). In some embodiments, the straps 84 can include locking mechanisms (not shown) to maintain the straps 84 in position when tightened. For example, the straps 84 can include ratcheting mechanisms, buckles, or other suitable locking mechanisms to keep the straps 84 in a tightened position when pulled.

Generally, the straps 12, 14, the supporting members 18, 20, and the fastening mechanisms can enable the pelvic binder 10 to distribute loads across, for example, its superior and inferior borders (e.g., the first strap 12 and the second strap 14) to provide sufficient pelvic compression while still leaving areas of pelvic region accessible for medical procedures. For example, as shown in FIGS. 5-7, similar to the pelvic binder 10 of FIGS. 1-2, the pelvic binder 10a can include an open region 48 partially defined between the first portion 40 and the second portion 42 of the first strap 12 (e.g., inside the "v" shape). This open region 48 can permit access to the abdomen adjacent the pubic symphysis 50 of the patient for, e.g., a midline laparotomy procedure or preperitoneal packing. The open region 48 provides access for such procedures while maintaining stability of the pelvis, that is, without requiring modification of the pelvic binder 10a, such as loosening, moving, or removing any straps. Accordingly, the pelvic binder 10a generally does not extend above or over the pubic symphysis 50 to allow access to the open region 48. Furthermore, access to the urethra for Foley catheter insertion can be available beneath the pelvic binder 10.

Additionally, in some embodiments, the pelvic binder 10a can include a first opening 52 defined between the first strap 12, the second strap 14, the fastening member 70, and the first supporting member 18. The pelvic binder 10a can also include a second opening 54 defined between the first strap 12, the second strap 14, the fastening member 70, and the second supporting member 20. The openings 52, 54 can each permit access to one of the common femoral artery and the common femoral vein along the first side 28 or the second side 30 of the patient, respectively. The openings 52, 54 provide access for such procedures while maintaining stability of the pelvis, that is, without requiring modification of the pelvic binder 10a, such as loosening, moving, or removing any straps or material. For example, FIG. 6 illustrates accessible locations 58, 60 of the femoral artery and femoral vein, respectively, within the second opening 54. Furthermore, such vascular access can be obtained by a medical professional or an autonomous device (as described above with respect to the pelvic binder 10 of FIGS. 1 and 2).

As described above, vascular access during pelvic stabilization can be beneficial to permit, for example, central venous line insertion or REBOA procedures. The pelvic binder 10a of some embodiments, by providing the openings 52, 54, is thus REBOA-compatible. Additionally, in some embodiments, to better accommodate interventional radiology procedures (such as REBOA, angiography, or endovascular embolization), the pelvic binder 10a can be made of radiolucent material.

In some embodiments, as shown in FIG. 7, the pelvic binder 10a can further comprise one or more loops 64 coupled to and extending below the second strap 14 (e.g., at least the horizontal section 32 of the second strap 14). For example, similar to the loops 64 described above with respect to the pelvic binder 10 of FIG. 1, two loops 64 can be coupled to the second strap 14 and configured to wrap around the buttocks of the patient (e.g., similar to a jock strap). Each of the loops 64 can run from a posterior lateral part of the pelvic binder 10a to the anterior, medial part of the pelvic binder 10a. As a result, the loops 64 can provide additional stabilization and, in some embodiments, can also prevent of migration of a traction splint attachment.

In some embodiments, one or more of the first strap 12, the second strap 14, the first supporting member 18, and the second supporting member 20 can include one or more attachment mechanisms 62 configured to couple an attachment to the pelvic binder 10a. These attachment mechanisms 62 can be similar to those described above with respect to FIG. 1 and can act as docking sites for different attachments (such as adjuncts for resuscitation). As such, any of the above-described attachments (e.g., vascular access device, femoral traction splint, restraints, etc.), can be coupled to the attachment mechanisms 62 of the pelvic binder 10a.

Accordingly, similar to the pelvic binder 10 of FIGS. 1-2, the pelvic binder 10a of FIGS. 5-7 can provide compression for pelvic fractures and is configured to distribute loads across its superior and inferior borders in order to leave body regions free for CFV or CFA access or abdominal access for midline laparotomies or preperitoneal packing. The pelvic binder 10a can further serve as a base for a traction splint (e.g., for femur fractures), an autonomous vascular access device (to assist vascular access), restraints, and/or other attachments.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A device used for stabilizing the pelvis of a patient, the device comprising:
   a first strap configured to substantially surround the patient at a first location adjacent the pelvis, the first strap including:
      a first horizontal section configured to be positioned adjacent a back side of the patient, and
      a second angled section configured to be positioned adjacent a front side of the patient;
   a second strap configured to substantially surround the patient at a second location adjacent the pelvis and below the first strap, the second strap including:
      a first horizontal section configured to be positioned adjacent the back side of the patient, and
      a second angled section configured to be positioned adjacent the front side of the patient,
   wherein the first horizontal section of the first strap and the first horizontal section of the second strap are configured to be positioned vertically equidistant from greater trochanters of the patient; and
   a third strap positioned between the first strap and the second strap and coupled to the second angled sections of the first strap and the second strap.

2. The device of claim 1 and further comprising a first supporting member coupled between the first strap and the second strap and configured to be positioned adjacent a first side of the patient adjacent the anterior superior iliac spine.

3. The device of claim 2 and further comprising a second supporting member coupled between the first strap and the second strap and configured to be positioned adjacent a second, opposite side of the patient adjacent the anterior superior iliac spine.

4. The device of claim 3, wherein the first horizontal section and the second angled section of the first strap are configured to meet at the first supporting member along the first side of the patient and the second supporting member along the second side of the patient.

5. The device of claim 3, wherein at least one of the first strap, the second strap, the first supporting member, and the second supporting member includes an attachment mechanism.

6. The device of claim 5, wherein the attachment mechanism is coupled to one of the first strap and the second strap and is configured to be coupled to a vascular access device configured to access one of the femoral artery and the femoral vein of the patient when the device is positioned around the pelvis.

7. The device of claim 5, wherein the attachment mechanism is coupled to one of the first supporting member and the second supporting member and is configured to be coupled to a femoral traction splint.

8. The device of claim 3, wherein the second angled section of the first strap includes a first portion that extends diagonally from the first supporting member to the third strap and a second portion that extends diagonally from the second supporting member to the third strap.

9. The device of claim 8 and further comprising an open region partially defined between the first portion and the second portion configured for permitting access to the pubic symphysis of the patient for a midline laparotomy procedure when the device is positioned around the pelvis.

10. The device of claim 3 and further comprising a first opening defined between the first strap, the second strap, the third strap, and the first supporting member, the first opening configured for permitting access to one of the femoral artery and the femoral vein along the first side of the patient.

11. The device of claim 3 and further comprising a second opening defined between the first strap, the second strap, the third strap, and the second supporting member, the second opening configured for permitting access to one of the femoral artery and the femoral vein along the second side of the patient when the device is positioned around the pelvis.

12. The device of claim 1, wherein the third strap is adjustable and configured to pull the first strap and the second strap toward each other to form the second angled sections of the first strap and the second strap and to tighten the device around the pelvis.

13. The device of claim 1, wherein the third strap is removably coupled to at least one of the first strap and the second strap.

14. The device of claim 1, wherein the third strap is configured to be positioned adjacent to and extend below the pubic tubercles of the patient.

15. The device of claim 1, wherein the first horizontal section of the first strap and the first horizontal section of the second strap are configured to be positioned vertically equidistant from the greater trochanter of the patient when the device is positioned around the pelvis.

16. The device of claim 1 and further comprising a loop coupled to and extending below the second strap at an anterior location and a posterior location thereof, the loop configured to wrap around the buttocks of the patient when the device is positioned around the pelvis.

17. A device configured to be worn by a patient for stabilizing the pelvis of the patient, the device comprising:
a first strap configured to substantially surround the patient at a first location adjacent the pelvis;
a second strap configured to substantially surround the patient at a second location adjacent the pelvis below the first strap;
a fastening mechanism configured to fasten the first strap and the second strap around the pelvis;
a first supporting member coupled between the first strap and the second strap and configured to be positioned adjacent a first side of the patient adjacent the anterior superior iliac spine;
a second supporting member coupled between the first strap and the second strap and configured to be positioned adjacent a second, opposite side of the patient adjacent the anterior superior iliac spine,
wherein the second strap is configured to substantially surround the patient by extending directly from the first supporting member directly to the second supporting member; and
a first opening defined between the first strap, the second strap, the first supporting member, and the fastening mechanism, first opening configured for permitting access to one of the femoral artery and the femoral vein along the first side of the patient.

18. The device of claim 17 and further comprising a second opening defined between the first strap, the second strap, the second supporting member, and the fastening mechanism, the second opening configured for permitting access to one of the femoral artery and the femoral vein along the second side of the patient.

19. The device of claim 17, wherein the fastening mechanism includes:
a first member coupled between the first strap and the second strap along the first side of the patient,
a second member coupled between the first strap and the second strap along the second side of the patient, and
an adjustable fastener coupled to the first member and the second member and configured to pull the first member toward the second member to tighten the device around the pelvis.

20. The device of claim 17, wherein the fastening mechanism includes a third strap coupled to the first strap and the second strap, the third strap being adjustable and configured to pull the first strap and the second strap toward each other to tighten the device around the pelvis.

21. A device used for stabilizing the pelvis of a patient, the device comprising:
a first strap configured to substantially surround the patient at a first location adjacent the pelvis, the first strap including:
a first horizontal section configured to be positioned around an entire back side of the patient, and
a second angled section configured to be positioned adjacent a front side of the patient;
a second strap configured to substantially surround the patient at a second location adjacent the pelvis and below the first strap, the second strap including:
a first horizontal section configured to be positioned around the entire back side of the patient, and
a second angled section configured to be positioned adjacent the front side of the patient; and
a third strap positioned between the first strap and the second strap and coupled to the second angled sections of the first strap and the second strap.

* * * * *